(12) United States Patent
Taeubert et al.

(10) Patent No.: US 10,350,407 B2
(45) Date of Patent: Jul. 16, 2019

(54) ELECTRONIC HEAD AND ELECTRODE LINE

(71) Applicant: BIOTRONIK SE & Co. KG, Berlin (DE)

(72) Inventors: Kerstin Taeubert, Berlin (DE); Lisa Hinrichsen, Berlin (DE); Patrick Poplien, Berlin (DE); Hartmut Lenski, Zossen (DE); Thomas Guenther, Michendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/589,137

(22) Filed: May 8, 2017

(65) Prior Publication Data

US 2017/0239464 A1    Aug. 24, 2017

Related U.S. Application Data

(63) Continuation-in-part of application No. 14/520,859, filed on Oct. 22, 2014, now abandoned.

(60) Provisional application No. 61/910,442, filed on Dec. 2, 2013.

(51) Int. Cl.
*A61N 1/05* (2006.01)

(52) U.S. Cl.
CPC ......... *A61N 1/0568* (2013.01); *A61N 1/0565* (2013.01); *A61N 1/0575* (2013.01)

(58) Field of Classification Search
CPC ...... A61N 1/05; A61N 1/0565; A61N 1/0568; A61N 1/057
See application file for complete search history.

(56) References Cited

U.S. PATENT DOCUMENTS

| | | |
|---|---|---|
| 5,496,360 A | 3/1996 | Hoffmann et al. |
| 2004/0172117 A1 | 9/2004 | Hill et al. |
| 2008/0114230 A1 | 5/2008 | Addis |
| 2011/0005069 A1 | 1/2011 | Pianca |
| 2011/0024186 A1 | 2/2011 | Receveur et al. |
| 2011/0130818 A1 | 6/2011 | Chen |
| 2012/0065699 A1 | 3/2012 | Bedenbaugh |
| 2012/0102698 A1 | 5/2012 | Scott |

OTHER PUBLICATIONS

European Search Report and Notes to the European Search Report on European Patent Application No. EP 14 19 0627.1, dated Jan. 7, 2015 (8 pages).

*Primary Examiner* — Tammie K Marlen
(74) *Attorney, Agent, or Firm* — Buchanan Ingersoll & Rooney PC

(57) ABSTRACT

An electrode head of an implantable electrode line, the electrode head including an elongate housing which has a longitudinal axis. The elongate housing includes at least two housing parts, which are cylinder-segment-shaped at least in portions and are fixedly joined together to form the electrode head along the longitudinal axis.

18 Claims, 8 Drawing Sheets

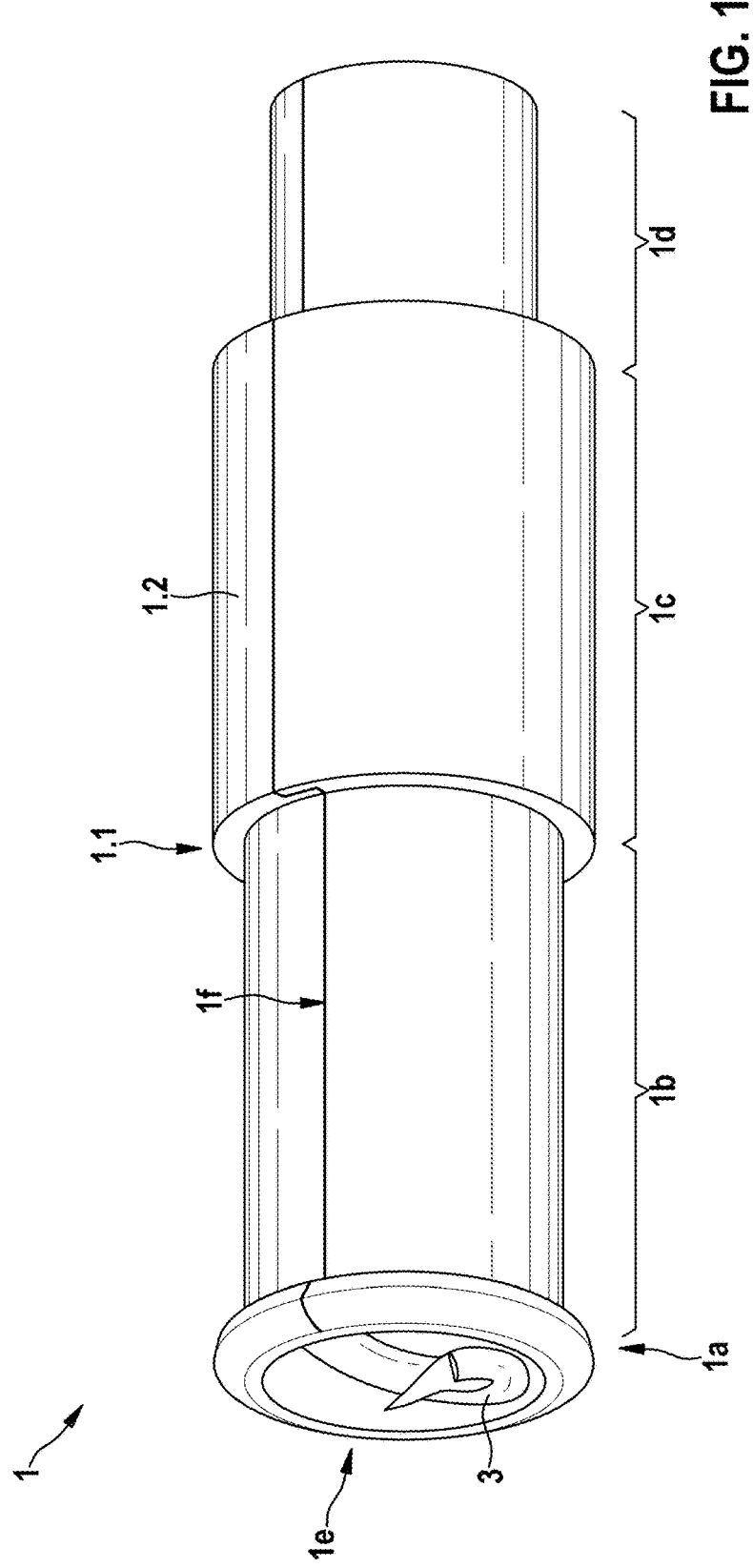

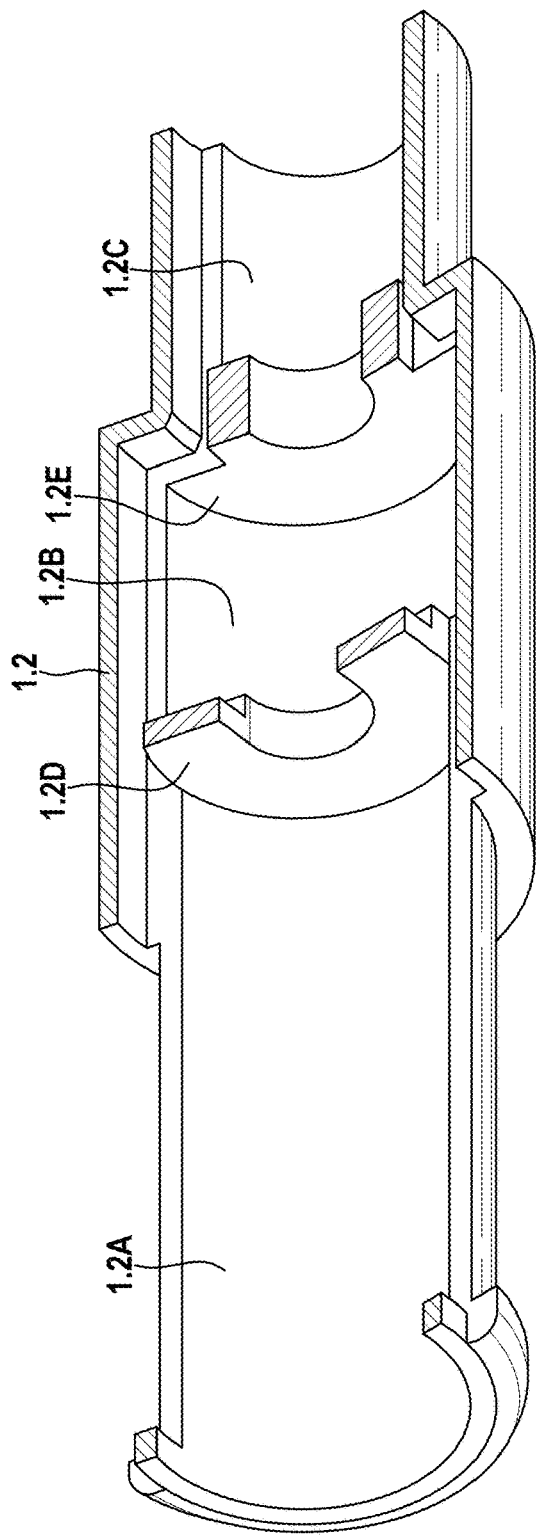

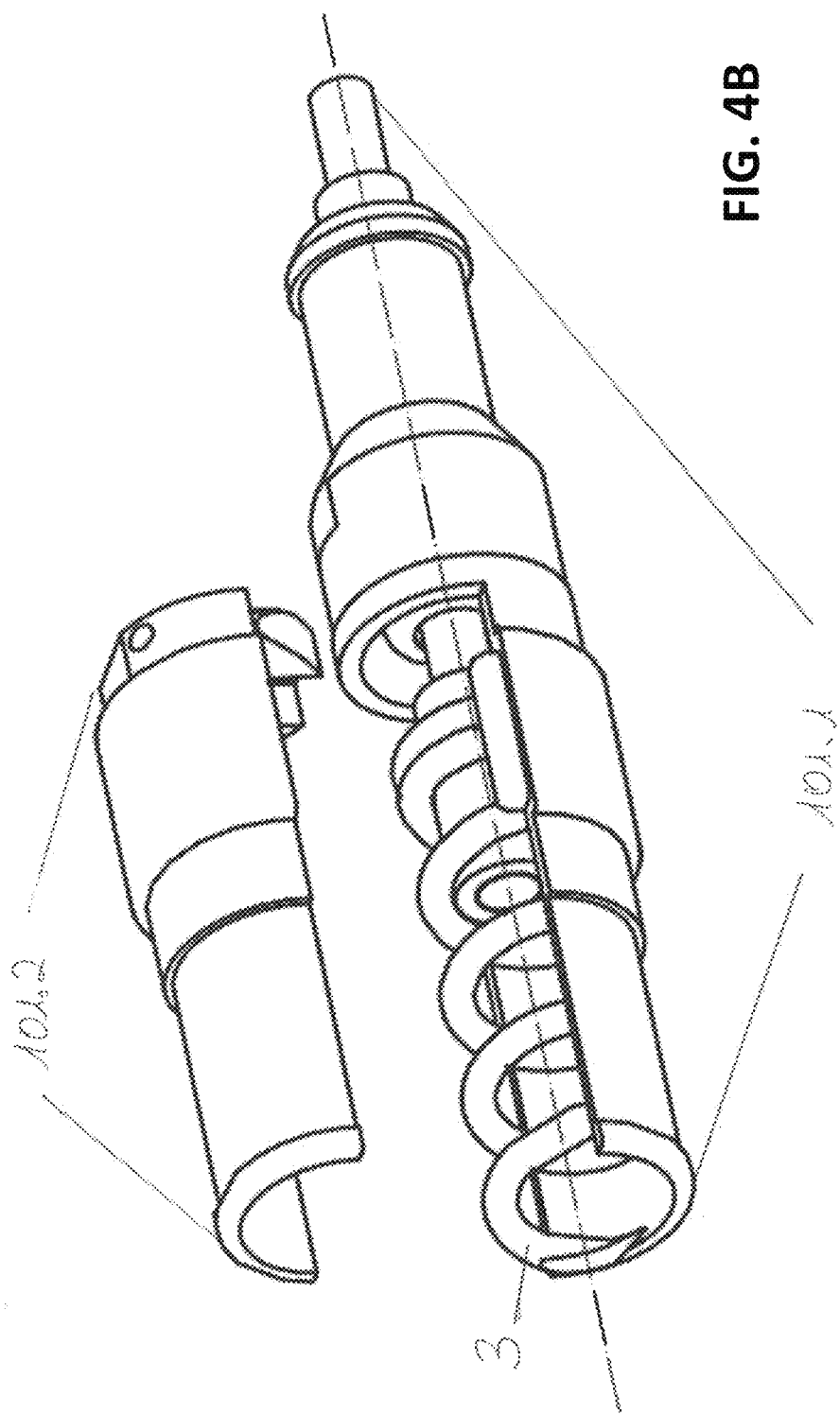

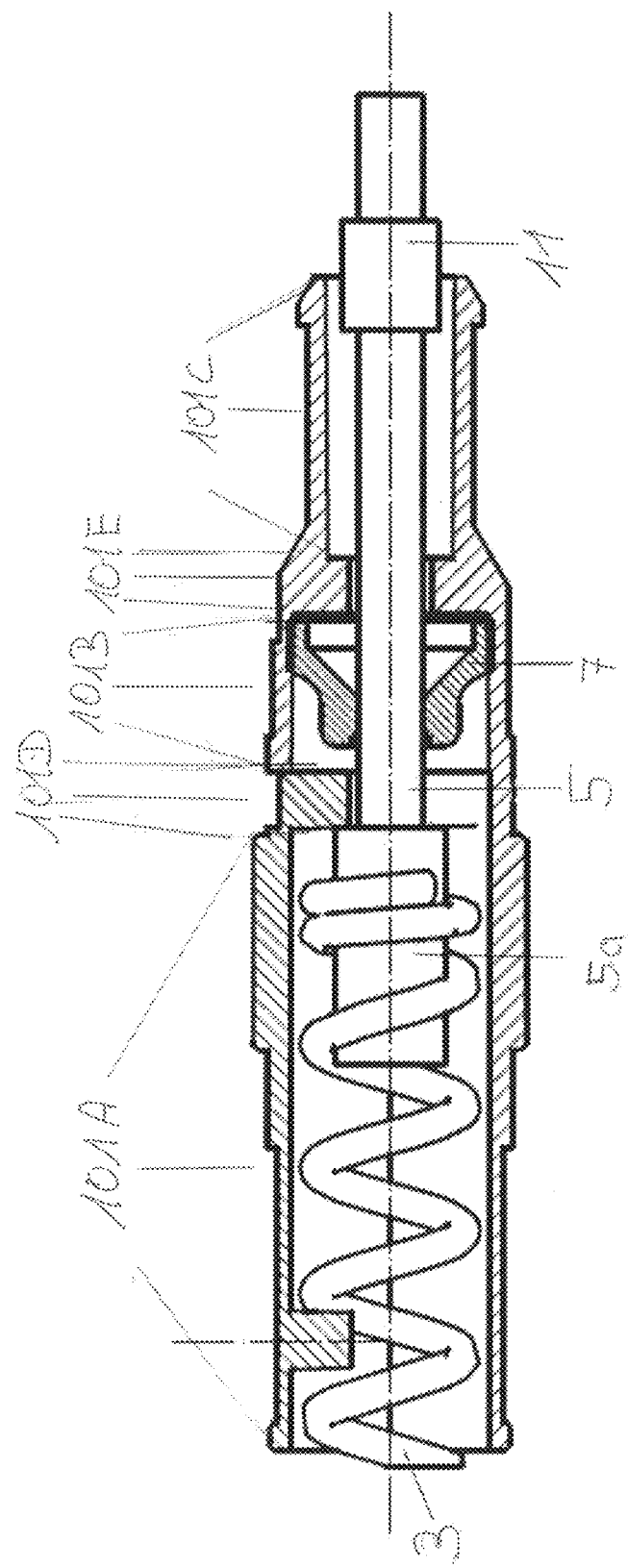

ELECTRONIC HEAD AND ELECTRODE LINE

CROSS-REFERENCE TO RELATED APPLICATIONS

This patent application is a continuation-in-part of U.S. patent application Ser. No. 14/520,859, filed on Oct. 22, 2014, now abandoned, which claims the benefit of U.S. Provisional Patent Application No. 61/910,442, filed on Dec. 2, 2013, which are hereby incorporated by reference in their entireties.

TECHNICAL FIELD

The present invention relates to an electrode head of an implantable electrode line, comprising a head housing. The present invention also relates to an electrode line.

BACKGROUND

Implantable electrode lines and respective electrode heads are a component of various electronic medical arrangements, specifically of cardiac pacemaker systems and implantable defibrillator systems, but also of arrangements for nerve or brain stimulation and also of arrangements for detecting action potentials and other electrical signals from a patient's body, for example, and are essential to the function of said arrangements. The reliable functioning of said arrangements, which in any case should also be safe for the patient, is therefore an indispensable prerequisite for their clinical use. Aspects such as sterilizability, easy handling and reasonable costs also play a key role in the development and the use of electrode lines and electrode heads.

For many applications, many electrode lines have to be designed such that their distal end can be securely fixed at the destination to, or in, a hollow organ (for example, the heart) or vessel of the patient. To meet this requirement, under consideration of the above-mentioned general requirements of electrode lines, comprehensive development efforts have been made over decades and a wide range of technical solutions proposed.

Among these, what are known as "screw heads" have achieved particular significance in practice, in which a helical coil is housed in the electrode head and, when the electrode line is implanted at the destination, is rotated out from the electrode head in a distal direction by the surgeon, and in doing so is simultaneously screwed into the tissue portion of the patient against which the electrode head abuts distally. Known screw heads consist of a plurality of interconnected cylindrical sleeves, usually made of a metal compatible with the body, and occasionally made of thermoplastics, such as PU (polyurethane) or PEEK (polyetheretherketone).

The present invention is directed toward overcoming one or more of the above-mentioned problems.

SUMMARY

With the present invention, an electrode head is provided which has the features of independent claim 1. Furthermore, an electrode line comprising an electrode head of this type is proposed. Expedient developments of the concept forming the basis of the present invention are disclosed in the dependent claims.

The present invention proceeds from the consideration of developing an electrode head (in particular, a screw head) which consists of few individual parts, which are also economical. The mechanism is to be designed here such that a fixing mechanism, in particular, (specifically a screw) can be produced in suitable geometric configuration and easily in terms of technology. The stringing together of individual parts produced by injection molding or machining, as is currently practiced, always leads to a large cumulative tolerance.

A key aspect of the solution according to the present invention lies in dividing the housing length-wise. Two cylinder-segment-shaped housing parts (individual shells) are thus produced and are shaped in such a way that all stops, centering means and advancing elements are formed by the tool. Due to the tool technology, it is ensured that there are no significant deviations in terms of dimension. Once the inner module has been inserted, the individual shells have to be fixedly interconnected.

The manufacturing aspect that all stops, centering means and advancing elements are formed by the tool together with the individual shells has the significant advantage that the parts can also be manufactured in large quantities and with maximum repeat accuracy. A further great advantage of this solution is that these elements are always arranged at the same distance from one another because these dimensions are predefined by the injection mold. The edge of the individual shells is designed here such that the shells are centered both in the longitudinal direction and in the transverse direction.

Insofar as reference is made here to the fact that the head housing comprises cylinder-segment-shaped housing parts, at least in portions, this is to include expressly housing parts of which the basic shape is that of a cylinder segment, but which on their inner and/or outer surface have molded or shaped portions which on the whole produce an inner or outer shape deviating from the cylinder-segment-shape. The distal end of the electrode head may additionally be conical or spherical or otherwise tapered, and in this respect may likewise deviate from a cylinder shape. In principle, such housing parts that have no dividing plane parallel to the longitudinal axis of the head housing, but a dividing plane inclined relative to the longitudinal axis or, for example, also a dividing plane that is turned in a spiraled manner, are also to be considered as belonging to the present invention.

An embodiment that is presently preferred, however, is that in which the head housing is joined from two shell parts having a semi-cylindrical outer contour and a dividing plane parallel to the longitudinal axis.

Furthermore, the housing parts, in particular, the semi-cylindrical shell parts, of the head housing are expediently welded or adhesively bonded together.

In a further embodiment, in particular, some of the housing parts are metal shaped parts, and in particular, metal stamped parts, formed from thin-walled sheet metal. In a further embodiment, in particular, some of the housing parts are plastic parts, and specifically injection molded parts. A head housing formed from a combination of metal and plastic parts also lies within the scope of the present invention.

In a further embodiment, the electrode head comprises a ring seal and/or an X-ray contrast ring, which, in one embodiment, is/are received in at least one second chamber of the electrode head, which is arranged proximally in relation to the first chamber. The X-ray contrast ring, which is made of metal, may simultaneously serve as a peripheral and closed sealing face for the seal between the shaft and housing.

In a further embodiment, the housing parts have a stepped outer diameter, in particular, in a proximal portion an outer diameter smaller than in a portion arranged distally in relation hereto. Specifically, this also includes embodiments with a lateral dimension stepped a number of times, for example, with a drug storage region in a portion of the outer surface. Specifically, the drug storage region is annular in this case, and the outer surfaces of the housing parts joined together have a recess corresponding to the dimensions of the annular drug storage region.

In a further embodiment, the electrode head has a plurality of chambers which are delimited by transverse wall pieces and which have a central aperture. In an expedient embodiment of a screw electrode head, three delimited chambers are provided, each of which receives at least one essential functional element of the screw electrode. However, more or less chambers are also contemplated. The inner module, in the normal case consisting of a fixing screw, stop sleeves, shaft, seal and coil, can be completely pre-assembled. Necessary stops on the shaft are visible and could be fixed in position relative to one another with maximum accuracy. The X-ray ring is then fitted on this module. The module thus completed is then inserted into the lower shell, the upper shell is fitted, and both half-shells are then interconnected.

In an embodiment of the proposed electrode line, the electrode head is joined by means of at least one connection tube piece to the electrode line body.

In a further embodiment of the proposed electrode line, the electrode head is joined by means of at least one resilient connection tube piece to the electrode line body.

In further embodiments of particular practical significance, the electrode line comprises an active fixing element, which, in particular, is received in a distally arranged first chamber of the electrode head. Specifically, the fixing element is formed as a rotatable and displaceable helical coil. Alternatively, however, it may also be formed as displaceable claws that can be splayed apart, movable fins or other fixing elements known per se, of which the implementation is compatible with the proposed design of the head housing and requires the provision of an actuation element or force transmission element (for example, a helical coil actuation shaft) within the line body of the electrode line.

Further features, aspects, objects, advantages, and possible applications of the present invention will become apparent from a study of the exemplary embodiments and examples described below, in combination with the Figures, and the appended claims.

DESCRIPTION OF THE DRAWINGS

Advantages and expedient features of the present invention will also emerge from the following description of an exemplary embodiment(s) with reference to the drawings, in which:

FIG. 1 shows a perspective external view of an electrode head according to an embodiment of the invention;

FIGS. 2A-2B show, respectively, a perspective view of the internal design (FIG. 2A) and of the inner wall of a half-shell of the electrode head from FIG. 1.

FIG. 5 shows a cross-section view of the alternate screw electrode head shown in FIG. 4A.

DETAILED DESCRIPTION

Figure 2A:
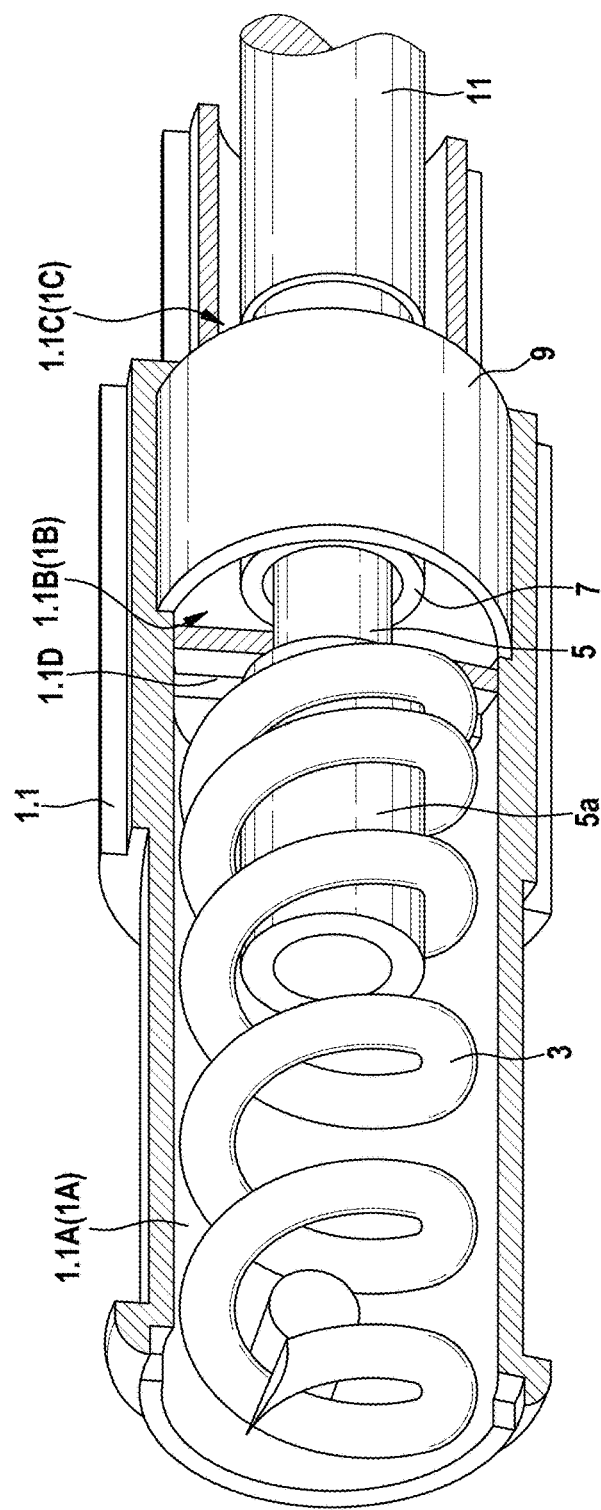

FIG. 1 shows a perspective illustration of a screw electrode head 1, which has a basic cylindrical shape, of an implantable pacemaker electrode line (see FIG. 3), of which the construction is shown in greater detail in FIGS. 2A-2B. At the distal end, the electrode head 1 has a rounded flange portion 1a of a first diameter, which is adjoined (in this order) by a first longer cylinder portion 1b of smaller diameter, a second longer cylinder portion 1c of larger diameter (which can be bigger, smaller or equal to the first diameter), and lastly a third longer cylinder portion 1d, again of reduced diameter again and also below the diameter of the first cylinder portion 1b. In addition, it can be seen that the electrode head 1 has an open distal end 1e, in which the distal end of a helical coil 3 can be seen. Furthermore, a continuous weld seam 1f can be seen and fixedly interconnects prefabricated half-shells 1.1 and 1.2 (not denoted separately here) of the electrode head 1 in an integrally bonded manner.

FIG. 2A shows the inner design of the electrode head 1, together with the first half-shell 1.1 of the head housing, and FIG. 2B shows the second half-shell 1.2 of the head housing, in each case again in a perspective illustration. For the sake of improved clarity, the above-referenced portions 1a to 1e of the outer contour of the head housing are not denoted again in FIGS. 2A-2B. It can be seen, however, that both half-shells 1.1, 1.2 have a division (naturally likewise in a half-shell-like manner) into three chamber segments 1.1A, 1.1B and 1.1C and 1.2A, 1.2B and 1.2C, respectively, adjoining one another in the longitudinal direction. The mentioned chamber segments are separated from one another by partition walls shaped primarily in the form of segments of a circle and having a central aperture, of which merely the more distal partition wall 1.1D of the first half-shell 1.1 can be seen in FIG. 2A, although both partition walls 1.2D and 1.2E can be seen in FIG. 2B.

When comparing the two drawings, it can be easily seen that the half-shells 1.1, 1.2 are not identical, but have different projections and returns or stops and centering means, both in the region of the distal flange and of two of the three stepped cylindrical regions and lastly also in the region of the partition walls. Inter alia, it is thus ensured that there are overlap regions of sufficient size in the wall of the head housing between the first and second half-shell so as to ensure high mechanical stability and tightness of the rear region of the head housing.

It can be seen from FIG. 2A how the helical coil 3 fills the distal chamber 1A of the electrode head 1 in the retracted state in its entire length and surrounds, via its proximal end, a ram 5a of a fixing screw actuation shaft 5, to which it is fastened (not visible here) in an integrally bonded manner (for example, by means of welding). In the second chamber 1B, the fixing screw actuation shaft 5 is surrounded by a ring seal 7 and an X-ray contrast ring 9 in such a way that the periphery of the chamber 1B is largely filled. In the third chamber 1C, a contact sleeve 11 for electrically contacting the conductor coil (not shown here) of the electrode line body with the ram 5a or the helical coil 3 can be seen.

Figure 3:
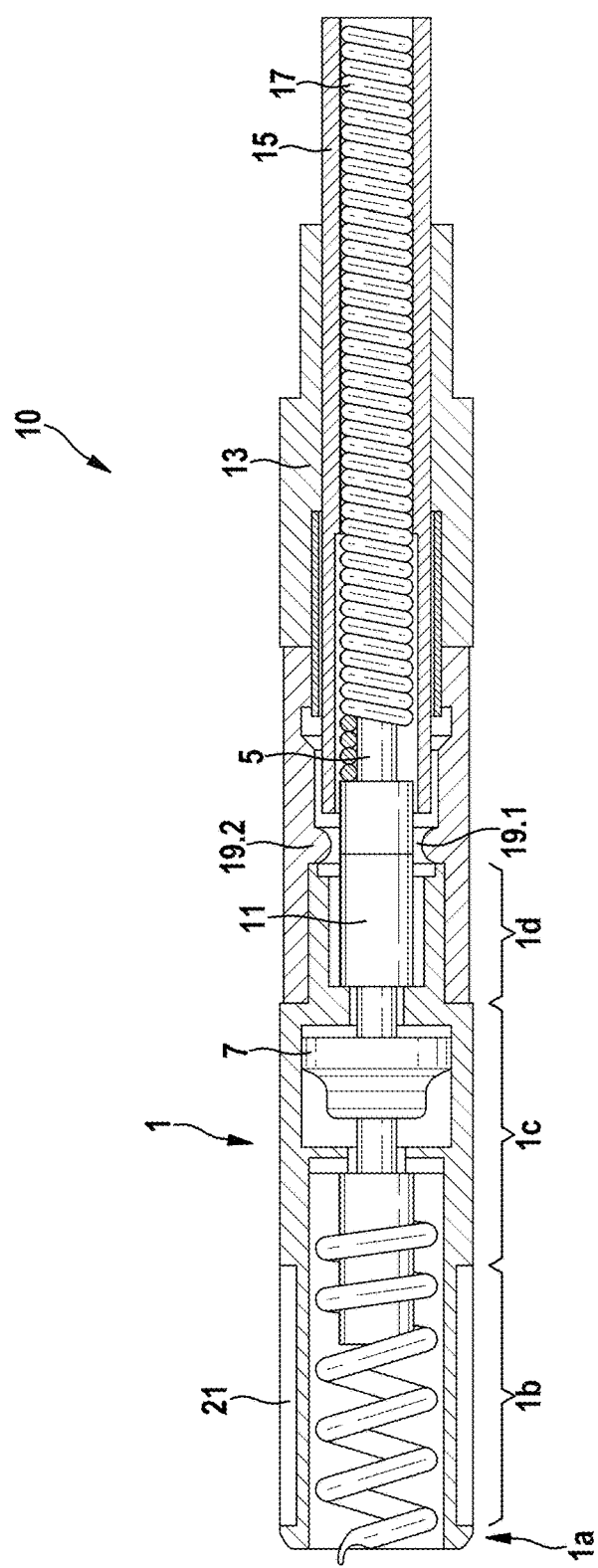
FIG. 3 shows a longitudinal section of the design of an electrode line provided with the electrode head according to FIGS. 1-2B (distal part).

FIG. 3 shows a longitudinal sectional illustration of the distal end region of an electrode line 10 provided with the electrode head 1 according to FIGS. 1-2B. Besides the electrode head 1, of which the outer shape and design are shown in FIGS. 1-2B and are described further above, the electrode line 10 comprises an outer line body (not shown here) or outer tube, an outer conductor coil (likewise not illustrated here) for contacting a ring electrode 13, and an inner conductor coil 17 arranged within an inner tube 15. The fixing screw actuation shaft 5, already mentioned above, is in turn placed in the interior of said coil, and the contact sleeve 11, likewise already mentioned further above, is attached to the end of said shaft.

The mechanical connection and simultaneous seal between the electrode head 1 and the line body of the line 10 distally in relation to the ring electrode 13 is produced by an inner PTFE (polyetrafluoroethylene—Teflon) tube 19.1 and a substantially likewise tubular outer silicone connection piece 19.2. Whereas the PTFE tube 19.1 is arranged within the proximal chamber 1C of the electrode head 1 and extends beyond a distal region of the inner conductor coil 17, the silicone connection piece 19.2 surrounds a distal end portion of the ring electrode 13 as well as the outer wall of the proximal chamber 1C (or, on the basis of the external view, the proximal cylinder portion 1d) of the electrode head 1 and interconnects these. Suitably shaped fixing ring portions, or locking portions, in the inner wall of the silicone connection piece 19.2 or the outer wall of the PTFE tube 19.1, and optionally additional fixing rings or other fixing means, contribute to secure fixing of the interconnected parts in the longitudinal direction of the electrode line in a manner known per se.

Specific attention should be paid in FIG. 3 to the complete illustration of the ring seal 7, of which only a distal end-face portion can be seen in FIG. 2A. It can be seen that the outer contour of the ring seal 7 is stepped or chamfered a number of times. Furthermore, a hollow-cylindrical drug storage region 21 is illustrated here in the region of the distal cylinder portion 1B of the electrode head 1 and (again in a manner known per se) serves to store and continuously dispense, in an ongoing manner, an anti-inflammatory steroid when the electrode line is implanted. When the half-shells are already fixedly connected to the cylindrical electrode head 1, the drug store in the form of a hollow cylinder 21 is slid over and fastened in the distal region.

In the shown embodiment, the electrode head 1 is preferably manufactured from PEEK half-shells, however PU half-shells or housing parts formed from another polymer that can be used in implanted parts can also be manufactured alternatively. In principle, the manufacture from a biocompatible metal, such as, for example, titanium or a titanium alloy or high-grade steel, is also considered, wherein special design provisions have to be made, however, in order to ensure the radiopacity of the length by which the helical coil is screwed out, and specific spring ranges, which are not provided in the above-described embodiment, would possibly have to be provided.

The embodiment of the present invention is not limited to the above-described examples and high-lighted aspects, but the present invention can also be implemented in a large number of modifications within the capabilities of a person skilled in the art.

Figure 4A:
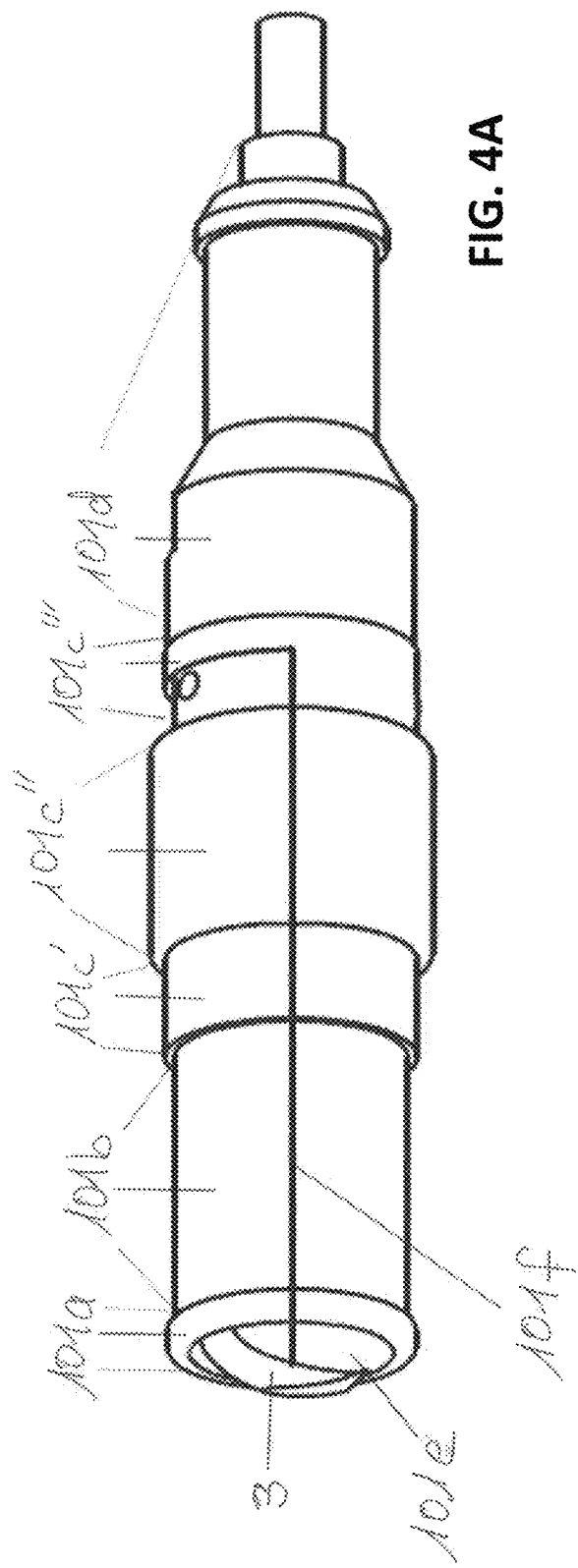
FIGS. 4A (closed shell) and 4B (open shell) show perspective illustrations of an alternate screw electrode head according to an additional embodiment of the present invention.
Figure 6:
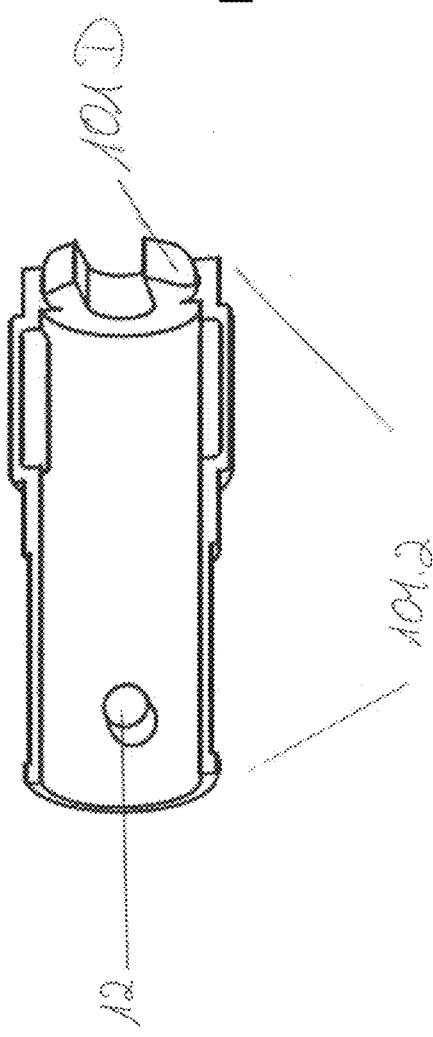
FIG. 6 shows an interior view of the shell part of the alternate screw electrode head shown in FIG. 4B.

FIGS. 4A (closed shell) and 4B (open shell) show a perspective illustration of an alternative screw electrode head 101, which has a basic cylindrical shape of an implantable pacemaker electrode line, of which the construction is shown in greater detail in FIGS. 5-6. At the distal end, the electrode head 101 has a rounded flange portion 101a of a first diameter, which is adjoined (in this order) by a first longer cylinder portion 101b of smaller diameter, a second longer cylinder portion 101c of larger diameter (which can be bigger, smaller or equal to the first diameter), and lastly a third longer cylinder portion 101d, again of reduced diameter and also below the diameter of the first cylinder portion 101a. The second longer cylinder portion 101c of larger diameter can consist of three cylinder portions 101c', 101c'' and 101c''', where the diameter of the cylinder portions 101c' and 101c''' is smaller or equal compared to the diameter of the cylinder portion 101c'', but the diameter of the cylinder portion 101c' is bigger than the diameter of the rounded flange portion 101a and also bigger than the diameter of the cylinder portion 101b. The diameter of the cylinder portion 101c''' is bigger than the diameter of the cylinder portion 101d. In addition, it can be seen that the electrode head 101 has an open distal end 101e, in which the distal end of a helical coil 3 can be seen. Furthermore, a continuous interface 101f, i.e., a weld seam or groove, can be seen where the prefabricated first shell part 101.1 and the second shell part 101.2 of the electrode head 101 are put together.

FIG. 5 shows the inner design of the electrode head 101, together with the first shell part 101.1 and the second shell part 101.2 of the head housing, and FIG. 6 shows the second shell part 101.2 of the head housing, in each case again in a perspective illustration. For the sake of improved clarity, the above-referenced portions 101a to 101e of the outer contour of the head housing are not denoted again in FIGS. 5-6. It can be seen in FIG. 5, however, that the housing of the head 101, formed out of the shell parts 101.1, 101.2, has a division (naturally likewise in a half-shell-like manner) into three chamber segments 101A, 101B and 101C, adjoining one another in the longitudinal direction. The mentioned chamber segments are separated from one another by partition walls shaped primarily in the form of segments of a circle or a ring and having at least a central aperture, of which both partition walls 101D and 101E can be seen in FIG. 5. In FIG. 6, merely the more distal partition wall 101D can be seen, because it is connected to the second shell part 101.2. The two shell parts 101.1 and 101.2 can be held together by one or two rings which can be slid over the cylinder parts 101c' and 101c'''. The rings can preferably manufactured from PEEK, PU or from another polymer that can be used in implanted parts. In principle, the manufacture from a biocompatible metal, such as, for example, titanium or a titanium alloy such as Platinum/iridium or high grade steel, is also considered. In addition, at least one of the rings can be an X-ray contrast ring, consisting at least in parts of a radiopaque material such as, i.e., Platinum/iridium. In addition or alternatively, the housing parts, in particular, the first and second shell parts 101.1 and 101.2, of the head housing are expediently welded or adhesively bonded together.

When comparing the two drawings, it can be easily seen that the half-shells 101.1, 101.2 are not identical, but have different projections and returns or stops and centering means, both in the region of the distal flange and of two of the three stepped cylindrical regions and lastly also in the region of the partition walls. Inter alia, it is thus ensured that there are overlap regions of sufficient size in the wall of the head housing between the first and second half-shell so as to ensure high mechanical stability and tightness of the rear region of the head housing. Due to the asymmetric form of the two shell parts 101.1 and 101.2, it is sufficient if the two shell parts 101.1 and 101.2 are held together by one or two rings which can be slid over the cylinder parts 101c' and 101c'''. In this case the housing parts, in particular, the first and second shell part 101.1 and 101.2, of the head housing do not necessarily need to be welded or adhesively bonded together. It can be seen from FIG. 6, that the second shell part has a pin 12 so that the helical coil acting as a fixation screw can be rotated out from the head housing in distal direction.

Figure 7:
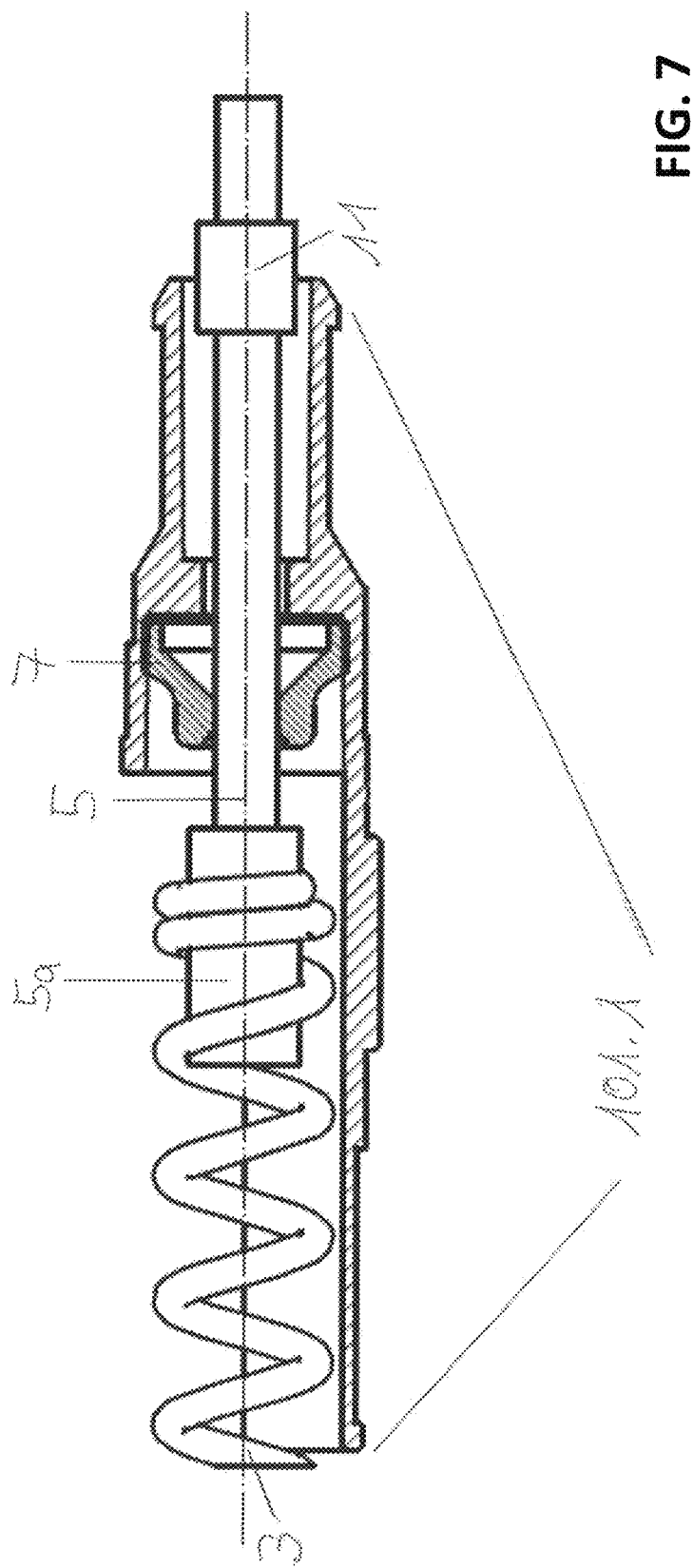
FIG. 7 shows a cross-sectional view of the alternate screw electrode head according to FIG. 5, with the shell part removed.

It can be seen from FIGS. 5 and 7 how the helical coil 3 fills the distal chamber 101A of the electrode head 101 in the retracted state in its entire length and surrounds, via its proximal end, a ram 5a of a fixing screw actuation shaft 5, to which it is fastened (not visible here) in an integrally bonded manner (for example, by means of welding). In the second chamber 101B, the fixing screw actuation shaft 5 is surrounded by a ring seal 7 in such a way that the periphery of the chamber 101B is largely filled. In the third chamber 101C, a contact sleeve 11 for electrically contacting the conductor coil (not shown here) of the electrode line body with the ram 5a or the helical coil 3 can be seen.

One or more of the helical coil 3, the fixing screw actuation shaft 5 and the ram 5a of the fixing screw actuation shaft 5 can consist at least in part of a radiopaque material. In case both rings are made as X-ray contrast rings and at least the ram 5a of the fixing screw actuation shaft 5 consists at least in part of a radiopaque material, it is possible to inspect how far the helical coil acting as a fixation screw has been rotated out from the head housing in distal direction.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An electrode head of an implantable electrode line, comprising:
   an elongate head housing which has a longitudinal axis and comprises two shell parts, a first shell part comprises a cylindrical outer contour in a proximal region and a half-cylindrical outer contour in a distal region, a second shell part has a half-cylindrical outer contour, the elongate head housing having a dividing plane parallel to the longitudinal axis, the first and the second shell parts are configured to be fixedly joined together, wherein the elongate head housing has a plurality of chambers delimited by transverse wall pieces, each transverse wall piece shaped in a form of a segment of a circle, each transverse wall piece extending from at least one inner surface of the two shell parts and having a central aperture when the two shell parts are fixedly joined together so that the chambers are separated from one another by the transverse wall pieces.

2. The electrode head as claimed in claim 1, wherein the two shell parts of the head housing are welded or adhesively bonded to one another.

3. The elegy trade head as claimed in claim 1, wherein the two shell parts of the head housing are held together by one or two rings which can be slid over the two shell parts without welding or adhesively bonding the two shell parts to one another.

4. The electrode head as claimed in claim 1, wherein at least a portion of the head housing comprises metal stamped parts.

5. The electrode head as claimed in claim 1, wherein at least a portion of the head housing comprises injection molded parts made of PEEK.

6. The electrode head as claimed in claim 1, wherein at least a portion of the head housing has a stepped outer diameter, such that in a proximal portion an outer diameter is smaller than in a portion arranged distally in relation to the proximal portion.

7. The electrode head as claimed in claim 1, wherein the elongate head housing further comprises an open distal and/or proximal end.

8. The electrode head as claimed in claim 1, further comprising a drug storage region in a portion of an outer surface of the elongate head housing.

9. The electrode head as claimed in claim 8, wherein the drug storage region is annular and outer surfaces of the two shell parts joined together have a recess corresponding to dimensions of the drug storage region.

10. An electrode line comprising:
    an elongate flexible electrode line body; and
    an electrode head as claimed in claim 1 attached distally to the electrode line body.

11. The electrode line as claimed in claim 10, wherein the electrode head is attached by means of at least one resilient connection tube piece to the electrode line body.

12. The electrode line as claimed in claim 10, further comprising an active fixing element which is received in a distally arranged first chamber of the electrode head.

13. The electrode line as claimed in claim 12, wherein the fixing element s formed as a rotatable and displaceable helical coil.

14. The electrode line as claimed in claim 12, further comprising a ring seal which is arranged in at least one second chamber of the electrode head arranged proximally in relation to the first chamber.

15. The electrode as claimed in claim 12, further comprising an X-ray contrast ring which is arranged in at least one second chamber of the electrode head arranged proximally in relation to the first chamber.

16. The electrode head as claimed in claim 1, wherein the plurality of chambers comprises three chambers.

17. The electrode head as claimed in claim 1, wherein the first shell part includes a first transverse wall piece in the proximal region having the cylindrical outer contour, wherein the second shell part includes a second transverse wall piece at a proximal end thereof, and wherein the first and second transverse wall pieces form different chambers in the head housing when the two shell parts are fixedly joined together.

18. The electrode head as claimed in claim 1, wherein the electrode head is configured to be implanted in a human body.

* * * * *